United States Patent [19]

Albanese et al.

[11] Patent Number: 5,637,762

[45] Date of Patent: Jun. 10, 1997

[54] 5H-PHENYL-3,13-DISULFONATODIBENZO-PHOSPHOLE AND A PROCESS FOR ITS PREPARATION

[75] Inventors: Guido Albanese, Munich; Rainer Manetsberger, Wielenbach; Wolfgang A. Herrmann, Freising; Rochus Schmid, Munich, all of Germany

[73] Assignee: Hoechst Aktiengesellschaft, Germany

[21] Appl. No.: 538,012

[22] Filed: Oct. 2, 1995

[30] Foreign Application Priority Data

Sep. 30, 1994 [DE] Germany .................. 44 35 171.2

[51] Int. Cl.$^6$ ...................................... C07F 9/50
[52] U.S. Cl. ............................................ 562/35
[58] Field of Search ................................. 562/35

[56] References Cited

U.S. PATENT DOCUMENTS 4,483,802  11/1984  Gartner .

FOREIGN PATENT DOCUMENTS 133410A    2/1985   European Pat. Off. .
0575785   12/1993   European Pat. Off. .

OTHER PUBLICATIONS

Copy of Angew, Chem. Int. Ed. Engl. 1995; vol. 34 (7); pp. 811–813 Univ. Muenchen, Germany.

Primary Examiner—Gary Geist
Assistant Examiner—Jean F. Vollano
Attorney, Agent, or Firm—Bierman, Muserlian and Lucas LLP

[57] ABSTRACT

5H-phenyl-3,13-disulfonatodibenzophosphole and a process for its preparation.

10 Claims, No Drawings

5H-PHENYL-3,13-DISULFONATODIBENZO-PHOSPHOLE AND A PROCESS FOR ITS PREPARATION

Complex compounds which have a metal from group VIII of the Periodic Table of the Elements as the central atom and as ligands of phosphorus (III) compounds, for example phosphines, phosphites or phospholes and optionally in addition further groups capable of forming complexes, have recently gained increasing importance as catalysts. Thus, the reaction practiced industrially on a large scale of hydroformylation of olefins with synthesis gas to produce aldehydes is carried out in the presence of catalyst systems comprising cobalt and, in particular, rhodium and triphenylphosphine. Catalysts based on phosphine-containing complex compounds have also proven useful for the reaction of methanol with synthesis gas to give higher alcohols, especially ethanol and propanol (homologation). In the cases mentioned, the ligands are usually present in excess, so that the catalyst system comprises complex compound and free ligand. In accordance with the solubility of the catalysts in organic media, the reactions are carried out in a homogeneous phase.

Instead of carrying out these reactions in a homogeneous phase, they can also, like other catalytic reactions, be carried out in heterogeneous reaction systems. This independent development is not limited to complex compounds of metals of group VIIIA, but also includes complex compounds of groups VIIA and IB of the Periodic Table of the Elements (IUPAC version) as catalysts. The use of catalysts dissolved in water has the advantage that they can be separated simply and gently from the water-insoluble reaction product. Processes which operate in accordance with this principle include, for example, a process described in DE-C-27 00 904 for the addition of hydrogen cyanide onto an unsaturated organic compound having at least one ethylenic double bond. Suitable catalysts for this reaction are nickel/TPPTS (TPPTS stands for tris (m-sulfonato-phenyl)phosphine), palladium/TPPTS or iron/TPPTS.

According to the process of DE-C-26 27 354, to prepare aldehydes by reacting olefins with carbon monoxide and hydrogen, use is made of rhodium in metallic form or in the form of one of its compounds together with a water-soluble phosphine, for example TPPTS, as catalyst. Further catalysts of the type mentioned and their use in various reactions such as hydrogenations, the allenealkyne coupling and the addition of amine onto double bonds, are described for example, in EP-A-372,313.

The two-phase processes with an aqueous catalyst solution have proven very useful on the industrial scale. Despite this, attempts are being made to bring the known processes closer to perfection and to transfer the reaction principle to other reactions. One way of achieving these objectives is to develop new catalysts, and in particular to modify the complex ligands. Thus, according to Hayashi et al., J. Mol. Catal., Vol. 6, (1970), p 1 ff., in the case of hydroformylation carried out with rhodium or cobalt as catalyst in a homogeneous phase, replacing diphenylphosphine by 5H-phenyldibenzophosphole leads to a considerable increase in the rate of reaction. The transfer of this procedure to the heterogeneous reaction system fails because it is impossible to sulfonate the phenyldibenzophosphole without oxidizing the phosphorus.

The sulfonation or aryl-containing mono-, di- and polyphosphines is carried out by a process which was originally developed for the sulfonation of triphenylphosphine (J. Chem. Soc., 1958, Vol. 281, p. 282). This process consists in reacting the phosphorous compound with oleum while heating, diluting the reaction product with water and neutralizing the diluted mixture with sodium hydroxide. The sodium salt of m-sulfonatophenyldiphenylphosphine crystallizes out from the sulfonation mixture. For the sulfonation of phosphines other than triphenylphosphine, this procedure is adapted individually, where appropriate, to the starting materials. The process, however, is not suitable for the sulfonation of 5H-phenyldibenzophosphole, which is sensitive to oxidation and is oxidized by sulfur trioxide to the phosphorus (V) compound.

OBJECTS OF THE INVENTION

It is an object of the invention to provide the novel compound, 5H-phenyl-3,13-disulfonato dibenzophosphole and a process for its preparation.

These and other objects of the invention will become obvious from the following detailed description.

THE INVENTION

The novel process of the invention for the preparation of the novel product, 5H-phenyl-3,13-disulfonatodibenzophosphole, comprises reacting 5H-phenyldibenzophosphole with an anhydrous mixture of sulfuric acid and orthoboric acid at 20° to 170° C. to form 5H-phenyl-3,13-disulfonatodibenzophosphole and recovering the latter. The preferred reaction temperature is 60° to 150° C.

Surprisingly, it has become evident that the use of an anhydrous mixture of sulfuric acid and orthoboric acid as sulfonating agent considerably reduces, or suppresses entirely, the formation of oxidation products from the oxidation-sensitive starting compound. A critical feature of the preparation process according to the invention is the use of an anhydrous mixture of sulfuric acid and orthoboric acid as sulfonating agent. Therefore, the sulfuric acid is advantageously employed in anhydrous form. In addition to this, it is necessary to remove the water of reaction which is formed in the sulfonating reagent $H_2SO_4/H_3BO_3$ in accordance with the equation

from the reaction mixture using water-binding substances.

A compound which has proven particularly suitable as a water binding agent is sulfur trioxide, which with water forms sulfuric acid, i.e. a compound native to the reaction. It is advantageously employed in the form of oleum. The water-binding reagent is preferably metered into the reaction mixture in proportion with the formation of water.

The other constituent of the sulfonating mixture, orthoboric acid, is used in its conventional commercial form and special purification is unnecessary. The acid is employed, relative to the P(III) atoms present in the phosphole, in approximately equimolar amounts, so that one mol of boric acid is present per mol of phosphorus atom. A slightly substoichiometric amount does not harm, but an excess is preferred. It is particularly advantageously to dissolve orthoboric acid in the sulfuric acid until saturation is reached.

The starting compound for the sulfonation, 5H-phenyldibenzophosphole, can be attained, for example, by the procedure disclosed in Chem. Ber., Vol. 95, (1962), p. 2563. Special purification is unnecessary unless required by the subsequent use of the sulfonated compounds, for example as a catalyst component.

It is advantageous to add the boric acid to the sulfuric acid even before introducing the phosphole, and to bind the water formed. The addition of the phosphole to the sulfonating reagent is made in portions at from 20° to 120° C., with rapid and uniform distribution of the phosphorus compound in the reaction mixture being ensured by, for example, stirring. It has proven suitable to employ the phosphorus compound in dissolved form, with anhydrous sulfuric acid preferably being used as solvent. The sulfonation takes place at temperatures in the range from 20° to 170° C., preferably from 60° to 150° C. To maintain as uniform a temperature as possible, it is advisable to stir the reaction mixture. The duration of the reaction depends on the reaction temperature and is usually from 5 to 50 hours.

After the reaction has ended, the reaction mixture is preferably diluted with oxygen-free water and worked up. According to a preferred process, the acidic aqueous solution of the sulfonation product is extracted with a solution of a water-insoluble amine in a water-insoluble organic solvent whereby a sulfonated product is obtained which is largely free from the orthoboric acid used in the sulfonation step.

In detail, in this manner of working up, the sulfonation mixture is admixed with the amount of oxygen-free water which is required to dilute the sulfuric acid present to 0.5 to 50% by weight, preferably to 25 to 35% by weight. The water-insoluble amine dissolved in a water-insoluble organic solvent is added to the dilute solution. The concentration of the amine solution is from 1.0 to 35% by weight, preferably from 10 to 30% by weight and, most preferably, from 13 to 25% by weight of amine, based in each case on the solution.

From 0.5 to 3.0 mole, preferably from 0.5 to 2.5 mole, of amine are used per equivalent of sulfonic acid. The use of excess amine ensures that the losses of phosphole are small. Although an excess of amine higher than that indicated above is possible, it leads to no improvement in the result of the separation or purification operation or in the yield.

After intensive mixing, two phases are formed. The aqueous phase of higher specific weight contains the sulfuric acid and almost all of the orthoboric acid, while the low-sulfate organic phase which is virtually free of orthoboric acid contains the amine salts of the sulfonated phosphine dissolved in the organic solvent. The two phases are separated from one another and the organic phase is optionally washed, for example with water, to remove any dissolved boric acid, and is then reacted with the solution of an inorganic base in water. In this context, the base is employed in an amount equivalent to the quantity of dissolved amine salt. Excess base should be avoided since it contaminates the end product. In this way, while recovering the water-insoluble amine, the aqueous solution of the sulfonated phenyldibenzophosphole is obtained and the amine is available for re-use.

The process described can be carried out either batchwise or continuously. The apparatus which finds application is that commonly used for separation such as counter-current extraction units.

Suitable water-insoluble amines which can be employed to carry out the process are water-insoluble, homo- and heterocyclic, aliphatic, aromatic, araliphatic and preferably open-chain, branched or unbranched aliphatic amines of 10 to 60, preferably 13 to 36, carbon atoms. Less suitable amines are those whose salts with the sulfonated phenyldibenzophosphole are of zero or limited solubility in the organic solvent. Examples of amines which have proven particularly suitable are tri-n-octylamine, tri-isooctylamine, tri-2-ethylhexylamine and tridodecylamine.

The amines are dissolved in a water-insoluble organic solvent and particularly suitable as solvents are aliphatic or aromatic hydrocarbons or hydrocarbon mixtures, for example toluene or kerosene, and also $C_4$ to $C_{20}$ alcohols and $C_8$ to $C_{20}$ ethers.

Bases suitable for transferring the sulfonated phenyldibenzophosphole to the aqueous phase are the hydroxides of the alkali metal and alkaline earth metals, especially an alkali metal hydroxide, ammonia, and also the alkali metal carbonates. By concentrating the aqueous solution to dryness, the corresponding salt of 5H-phenyl-3,13-disulfonatodibenzophosphole is obtained and from this salt, it is possible by ion exchange to prepare the free acid and also the salts of other metals.

Working up is advantageously carried out in the range of room temperature up to about 40° C. since higher temperatures give no advantages. The comments relating to the solubility of the amines and of the organic solvents in water are in this context related in each case to the temperatures at which the process is carried out.

5H-phenyl-3,13-disulfonatodibenzophosphole has proven useful as a component of catalyst systems such as those comprising rhodium or cobalt, for the hydroformylation of olefinically unsaturated compounds but also for other reactions by known methods.

In the following example, there are described several preferred embodiments to illustrate the invention. However, it should be understood that the invention is not intended to be limited to the specific embodiments.

EXAMPLE

Preparation and properties of 5H-phenyl-3,13-disulfonatodibenzophosphole.

(a) Sulfonation of 5H-phenyldibenzophosphole 10 ml of oleum (65% by weight $SO_3$) were added dropwise to a solution of 2.40 g (38.4 mmol) of orthoboric acid in 8 ml of concentrated sulfuric acid (96%), so that the resulting mixture had an $SO_3$ concentration of approximately 5.6% by weight. The excess $SO_3$ was removed in a high vacuum at 60° C. over the course of 45 minutes. Subsequently, 500 mg (1.9 mmol) of 5H-phenyldibenzophosphole (molar ratio of boric acid to phosphorus=20:1) were dissolved with stirring in the $H_2SO_4/H_3BO_3$ mixture and the mixture was reacted at 145° C. for 15 hours. The reaction mixture was then cooled, hydrolyzed with 20 ml of oxygen-free water and extracted with 4 ml of triisooctylamine in 30 ml of toluene. The organic phase was washed three times with 20 ml of water to remove the boric acid completely and then was extracted with 7.5M NaOH until a pH of 11.8 was established. Subsequently, the aqueous phase was neutralized with 3M $H_2SO_4$ and concentrated to dryness in vacuo. The solid which remained was extracted to obtain 852 mg, corresponding to 89% of theory, of the desired product as a vitreous white solid.

(b) Characterization of 5H-phenyl-3,13-disulfonatodibenophosphole as its $Na^+$ salt:

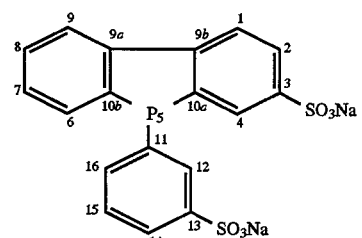

$^{31}P\text{-}\{^1H\}$-NMR ($D_2O$): $\delta17.42$; $^1H\text{-}^1H$-COSY-NMR ($D_2O$): $\delta=6.90$ (dt, $^3J_{HH}=7.3$ Hz, $^4J_{HH}=1.9$ Hz, 2H, H8, H9), 7.01 (tt, $^3J_{HH}$=7.7 Hz, $^4J_{HP}$=12.0 Hz, $^4J_{HH}$=1.2 Hz, 1H, H16), 7.06 (td, $^3J_{HH}$=7.7 Hz, $^4J_{HP}$=3.2 Hz, 1H, H 15), 7.20 (dd, $^3J_{HH}$=8.0 Hz, $^4J_{HP}$=4.4 Hz, 1H, H1), 7.32 (dt, $^3J_{HH}$=7.3 Hz, $^4J_{HH}$=1.9 Hz, 2H, H6, H7), 7.43 (dt, $^3J_{HP}$=14.0 Hz, $^4J_{HH}$=1.2 Hz, 1H, H12), 7.81 (dd, $^3J_{HH}$=8.0 Hz, $^4J_{HH}$=2.0 Hz, 1H, H2), 8.41 (dd, $^3J_{HP}$=14.0 Hz, $^4J_{HH}$=2.0 Hz, 1H, H4), 7.55 (ddd, $^3J_{HH}$=7.7 Hz, $^4J_{HH16}$=1.8 Hz, $^4J_{HH15}$=1.3 Hz, 1H, H14).

Various modifications of the product and process of the invention may be made without departing from the spirit or scope thereof and it is to be understood that the invention is intended to be limited only as defined in the appended claims.

What we claim is:

1. 5H-phenyl-3,13-disulfonatodibenzophosphole and salts thereof.

2. A process for the preparation of 5H-phenyl-3,13-disulfonatodibenzophosphole comprising reacting 5H-phenyldibenzophosphole at a temperature of 20° to 170° C. with an anhydrous mixture of sulfuric acid and orthoboric acid to obtain 5H-phenyl-3,13-disulfonatodibenzophosphole.

3. The process of claim 2 wherein the reaction is carried out at 60° to 150° C.

4. The process of claim 2 wherein water present in the mixture of sulfuric acid and orthoboric acid is removed with water-binding agents.

5. The process of claim 4 wherein the water-binding agent is sulfur trioxide.

6. The process of claim 5 wherein the sulfur trioxide is employed in the form of oleum.

7. The process of claim 2 wherein 5H-phenyldibenzophosphole is introduced into the anhydrous mixture of sulfuric acid and orthoboric acid as a solution in anhydrous sulfuric acid.

8. The process of claim 2 wherein orthoboric acid is employed in an at least equimolar amount based on 5H-phenyldibenzophosphole.

9. The process of claim 2 wherein the anhydrous mixture of sulfuric acid and orthoboric acid is saturated with orthoboric acid.

10. The process of claim 2 wherein after sulfonation has ended, the reaction mixture is admixed with an amount of water required to dilute the sulfuric acid present to 0.5 to 50% by weight, extracting the resulting aqueous solution with a solution of a water-insoluble amine in a water-insoluble organic solvent, 0.5 to 3 mol of the amine being employed per chemical equivalent of sulfonic acid, separating the organic phase and intimately contacting the aqueous solution with a base, separating the aqueous phase and recovering the sulfonated aryl-phosphine therefrom.

\* \* \* \* \*